United States Patent [19]
Rhodes

[11] Patent Number: 5,772,321
[45] Date of Patent: Jun. 30, 1998

[54] COMPENSATION FOR SPACIAL AND TEMPORAL TEMPERATURE VARIATIONS IN A THERMAL CONDUCTIVITY DETECTOR

[75] Inventor: Robert P. Rhodes, Lincoln University, Pa.

[73] Assignee: Hewlett-Packard Company, Palo Alto, Calif.

[21] Appl. No.: 548,037

[22] Filed: Oct. 25, 1995

[51] Int. Cl.$^6$ .................................................. G01N 25/18
[52] U.S. Cl. ........................ 374/44; 73/25.03; 73/25.05
[58] Field of Search ............................. 374/44; 73/25.03, 73/25.05, 61.76

[56] References Cited

U.S. PATENT DOCUMENTS

| | | |
|---|---|---|
| 4,389,876 | 6/1983 | Szonntagh . |
| 4,902,138 | 2/1990 | Goeldner et al. ........................ 374/44 |
| 5,379,630 | 1/1995 | Lacey . |

FOREIGN PATENT DOCUMENTS

| | | |
|---|---|---|
| 5-119003 | 2/1993 | Japan ...................................... 374/44 |
| WO93/02352A1 | 2/1993 | WIPO . |

OTHER PUBLICATIONS

UK Patent Office, Dec. 6, 1996, Examiner: Clarke, M.G.

*Primary Examiner*—George M. Dombroske
*Assistant Examiner*—Joseph L. Felber
*Attorney, Agent, or Firm*—Mark Z. Dudley

[57] ABSTRACT

A thermal conductivity detector includes a cavity wall defining a cavity for receiving a quantity of a sample fluid, the cavity wall being subject to a cavity wall temperature that is temporally and spatially variable, and a sensor located in the cavity and connected preferably in a bridge circuit configuration for providing a temperature sense signal. The sensor exhibits a resistance which is dependent on a temperature of the sensor. A first signal providing means includes reference means preferably in the form of first and second reference resistors located within first and second reference resistor cavities. The first and second reference resistors are connected to a reference voltage in a voltage divider network such that a node of the voltage divider network provides a temperature compensation signal that is representative of the average temperature of the cavity wall. Second signal providing means, connected to the balance nodes of the bridge circuit configuration, provide a temperature sense signal that is related to a change in resistance of the sensor resistor and thereby representative of the sensor temperature. The temperature compensation signal may optionally be conditioned by a voltage gain circuit and a voltage offset circuit to provide a temperature compensation signal. The temperature sense signal and the temperature compensation signal are provided to a third signal providing means wherein the temperature compensating signal is used to accurately compensate for changes in the temperature sense signal that are due to the temporal and/or spatial variations in the cavity wall temperature. In particular, the temperature compensation signal may represent an averaged value of at least two cavity wall temperatures, thus particularly compensating for the effect of a spatial temperature gradient in the cavity wall.

10 Claims, 6 Drawing Sheets

COMPENSATION FOR SPACIAL AND TEMPORAL TEMPERATURE VARIATIONS IN A THERMAL CONDUCTIVITY DETECTOR

FIELD OF THE INVENTION

This invention relates to thermal conductivity measurement devices, and in particular, to precision measurement devices for measuring the thermal conductivity of a fluid, such as a gas, to detect compounds within the fluid.

BACKGROUND OF THE INVENTION

Gas chromatographs are used to determine the chemical composition of a sample, which may be gaseous or a vaporized liquid. The term gas will hereinafter be used to include a vapor. In one type of gas chromatograph, a sample is sent through a separation column. A typical separation column is a long capillary tube with a coated interior. Different chemical compounds in the sample travel through the separation column at different rates and leave the separation column at different times. As compounds leave the separation column, they are carried by a carrier gas past a detector. The detector detects compounds in the carrier gas by measuring changes in the properties of the effluent gas. When a change in the gas property occurs, the timing of the change indicates the type of the compound passing the detector, and the magnitude of the change indicates the quantity of the compound.

One type of detector used with gas chromatographs is a thermal conductivity detector, which detects changes in the thermal conductivity of the effluent gas. When a compound is mixed with the carrier gas, the thermal conductivity of the mixture is usually different from that of the pure carrier gas. A thermal conductivity detector provides a measure of the change in the thermal conductivity of the carrier gas and thereby provides a measure of the presence and amount of various compounds.

Figure 1:
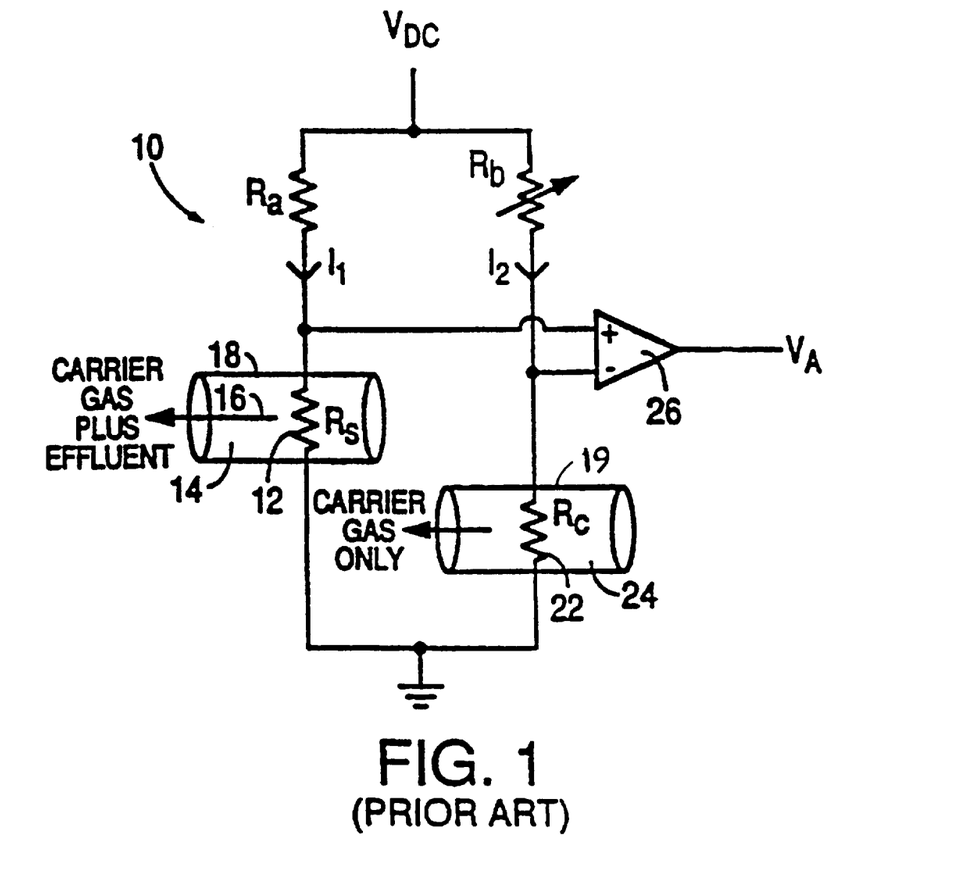
FIG. 1 is a schematic diagram of a prior art thermal conductivity detector.

FIG. 1 shows a typical prior art sensor circuit 10 used in a thermal conductivity detector of a gas chromatograph. The sensor circuit 10 includes a metal filament 12, such as a platinum wire, placed in a cavity 14. The effluent from a gas separation column along with a carrier gas fills the cavity 14 and flows along a path 16 past the filament 12. The filament 12 has a resistance $R_S$ which depends on its temperature and is heated using an electric current $I_1$. In the case of the filament 12 being a platinum wire, the resistance of the filament 12 is proportional to its temperature.

Heat generated by the filament 12 is removed partially by the flow of the effluent but primarily by thermal conduction through the gas to the cavity wall 18 of the cavity 14, thus lowering the resistance of the filament 12. By effectively measuring the change in resistance of the heated filament 12, the change in thermal conductivity of the flowing gas may be determined.

In some applications, problems arise that can cause the output of the sensor circuit 10 to change even if the composition of the gas remains constant. One problem is caused by spatial and temporal variations in the temperature of the cavity wall 18. With the sensitivity required of a detector, such variations may affect the detector. Changes in the voltage offset of the amplifiers used to measure changes in the resistance of filament 12 are still another problem.

One technique for attempting to avoid some of these problems is illustrated in FIG. 1, wherein the filament 12 is operated in a bridge circuit employing a control filament 22 which is ideally identical to the filament 12 and is located in a cavity 24 similar to the cavity 14 but containing only a pure carrier gas. A variable resistor $R_B$ is used to match the resistance of a fixed resistor $R_A$. A differential amplifier 26 detects an unbalance in the bridge. A DC voltage supply is used to heat the filaments 12, 22 to a temperature elevated above the temperature of the cavity walls 18, 19. If the thermal conductivity of the effluent in the cavity 14 is different from that of the pure carrier gas in cavity 24, the bridge becomes unbalanced, and a change in the amplifier's output voltage $V_A$ indicates the detection of a change in thermal conductivity of the gas in the cavity 14. Common mode temperature variations in the temperature of the block surrounding the cavities 14 and 24 as well as common mode temperature variations in the temperature of the carrier gas are expected to change the resistances of the filaments 12 and 22 equally, and thus not affect $V_A$.

However, the two different filaments 12 and 22 cannot be made exactly the same and therefore do not react identically to identical changes in their ambient environment. Even if the filaments 12 and 22 could be made to be initially identical, the properties of these devices may change with time, producing a bridge imbalance with common changes in the ambient environment of the filaments 12 and 22. Also, the filament 12 and the control filament 22 can be subject to a spatial temperature variations (i.e., a block temperature gradient). Thus, the filament 12 may experience a cavity wall temperature that is different than the cavity wall temperature that affects the control filament 22. As a result, the sensitivity and the accuracy of the detector output signal is less than desirable.

In another approach (not shown), only the sensor filament 12 is employed in a single cell; the control filament 22 is replaced by a fixed resistor. The analytical flow (the carrier gas plus effluent) along path 16 is modulated (made to alternate) with a flow of pure carrier gas. A sensor signal is then extracted from the signal output ($V_A$) by demodulation techniques. However, there can be loss of a sample constituent during a period of pure carrier gas flow. The detector output signal is therefore less accurate than desired, and the output signal is more susceptible to noise effects.

SUMMARY OF THE INVENTION

The present invention provides methods and structures for measuring thermal conductivity of a sample fluid contained in a sensor cavity. The measurement is made in a manner that compensates for the effects of spatial and/or temporal temperature variations in the cavity wall that defines the sensor cavity.

In particular, a thermal conductivity detector may be constructed according to the present invention to include a detector block having a cavity wall that defines a sensor resistor cavity for receiving a quantity of the sample fluid, the cavity wall being subject to a cavity wall temperature, and the cavity wall temperature being subject to temporal and spatial variations. A sensor resistor is located in the sensor resistor cavity. The sensor resistor exhibits a sensor resistance that is dependent on the temperature of the sensor resistor. A first signal providing means includes reference means located proximate to the cavity wall so as to be responsive to the temporal and spatial variations in the cavity wall temperature for providing a temperature compensation signal representative of at least one of the spatial variation and temporal variations. A second signal providing means, connected to the sensor resistor, provides a temperature sense signal that is related to the sensor resistance. A third signal providing means receives the temperature sense signal and the temperature compensation signal, and, in accordance with the temperature compensation signal, provides a detector output signal that is representative of the thermal conductivity of the sample fluid, the detector output signal being compensated for the effect of at least one of the spatial variation and the temporal variation in the cavity wall temperature. The contemplated thermal conductivity detector thereby offers greater sensitivity, accuracy, and reliability in comparison to the prior art.

DETAILED DESCRIPTION OF THE PREFERRED EMBODIMENTS

The apparatus and methods of the present invention provide improved accuracy in a thermal conductivity detector suitable for use in an analytical instrument. The terms "analysis" and "analytical" are meant broadly to include both qualitative and quantitative analytical methods, detection, or observation of physical or chemical parameters. Additionally, the apparatus and methods described herein may be applied to directly or indirectly effect compensation for the effects of variable ambient temperature on a resistive sensing element that may be present within a heated zone or cavity in an analytical instrument.

Chromatographic analysis of gaseous sample is the preferred mode of analysis according to the practice of the present invention, and the following description of the invention will be directed to a thermal conductivity detector intended for use in a gas chromatographic analytical system. However, the teachings herein may be applied to a thermal conductivity detector suitable for use in an analytical instrument for effecting a chromatographic analysis of multiple component gases and mixtures thereof capable of regulated flow. Moreover, it should be understood that the teachings herein are applicable to a thermal conductivity detector for use in instruments that operate using other analytical methods or that analyze other physical parameters and phenomena.

The basic mechanism underlying chromatographic analysis is the separation of a sample chemical mixture into individual components by transporting the mixture in a carrier fluid through a specially prepared separation column having a retentive media therein. The carrier fluid is referred to as the mobile phase and the retentive media is referred to as the stationary phase. The principal difference between liquid and gas chromatography is that the mobile phase is either a liquid or a gas, respectively. Liquid chromatography devices are capable of analyzing much heavier compounds than gas chromatography devices. However, gas chromatography detection techniques are more sensitive and therefore the present invention contemplates the use of a thermal conductivity detector in a gas chromatograph. For the purposes of clarity, only the detector portion of the contemplated gas chromatograph is illustrated.

In a gas chromatographic analysis, a sample of the subject mixture is injected into a fluid stream and passed through the separation column. Separation is due primarily to differences in the partial pressures of each sample component in the stationary phase versus the mobile phase. As the basic techniques for the preparation, separation, and detection of sample components are known to those skilled in the art, the description to follow will be directed primarily to the construction and operation of a novel thermal conductivity detector that is sensitive, accurate, reliable, and inexpensive.

Figure 2:
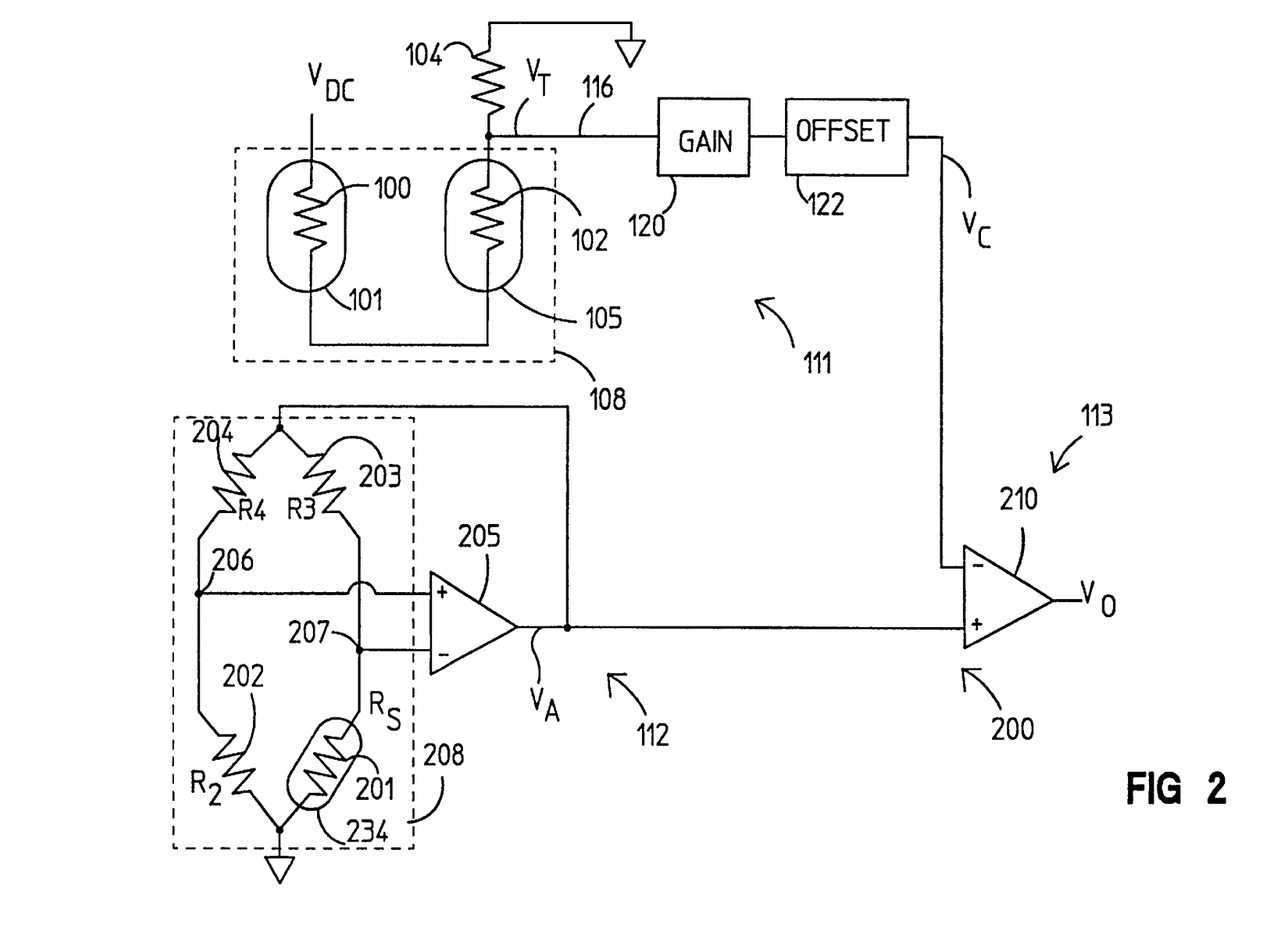
FIG. 2 is a simplified schematic diagram of a thermal conductivity detector constructed according to the present invention.

As illustrated in FIG. 2, a preferred embodiment of a thermal conductivity detector 200 may be constructed to include a first signal providing means 111 that includes a reference signal means 108 for providing a temperature compensation signal $V_C$. The first signal providing means 111 preferably includes a fixed reference voltage source $V_{DC}$ connected to the reference signal means 108 and a fixed resistor 104 having one leg connected to a ground potential. A second signal providing means 112 includes a sensor resistor 201 in a sensor resistor cavity 234. The reference signal means 108 comprises at least one but preferably a plurality of similarly-constructed reference resistors that are embedded or otherwise disposed in a detector block so as to be subject to the temperature of the cavity wall that defines the sensor resistor cavity 234. Accordingly, a first reference resistor 100 is provided in a first reference resistor cavity 101 and a second reference resistor 102 is provided in a second reference resistor cavity 105 within the detector block (embodiments of suitable detector blocks will be described in greater detail below with reference to FIGS. 3A–3C and 4).

A sample fluid stream, which typically includes one or more separated constituents of a sample borne by, for example, a carrier gas, flows through the sensor cavity 234. The sample fluid exhibits a varying thermal conductivity that is then measurable by detecting changes in the resistance $R_S$, and thus the temperature, of the sensor resistor 201. In the preferred embodiment, the power delivered to the sensor resistor 201 is controlled so as to maintain a constant temperature therein. Changes in the resistance $R_S$ are then discerned by monitoring changes in the power delivered to the sensor resistor 201. It should be noted that in a departure from the prior art, the sample fluid flow need not be subject to the modulation techniques as described hereinabove, nor is there any need for the use of a control filament in a cavity that receives a flow of carrier gas only.

The detector block is subject to a controlled temperature by temperature control apparatus (not shown) as known in the art. However, one may expect that the detector block, and in particular the cavity wall, are subject to two types of temperature variations: one that is distributed over time (temporal variation) and one that is distributed according to location within the detector block (spatial variation). The first signal providing means 111 may therefore be operated for providing a temperature compensation signal representative of at least one (and preferably both) of the spatial and temporal variations such that the effects of the temperature variation(s) on a detector output signal may be compensated. As will be described below, the contemplated temperature compensation signal is used in particular for compensating for the influence of such spatial and/or temporal variations on a temperature sense signal derived from the operation of the sensor resistor 201.

In a particular feature of the present invention, the first and second reference resistors 100, 102 are located with respect to sensor resistor cavity 234 such that the temperature of the cavity wall is predominant in influencing the temperatures of the first and second reference resistors 100, 102. That is, the detector block is intentionally constructed such that the temperature of the cavity wall is a substantial influence on the temperatures of the first and second reference resistors 100, 102 in comparison to the temperatures of other portions or regions of the detector block. To achieve this end, the detector block may be constructed such that the thermal impedance between the sensor resistor cavity 234 and the first and second reference resistors 100, 102 is substantially less than the thermal impedances between the first and second reference resistors 100, 102 and the remainder of the detector block. In some embodiments, the desired influence of the temperature of the cavity wall on the operation of the first and second reference resistors 100, 102 may be achieved by placement of the first and second reference resistor cavities 101, 105 such that they are located immediately adjacent the sensor resistor cavity 234 and are separated from the sensor resistor cavity 234 by a thin cavity wall. Thus, sufficient thermal impedances are effected between the first and second reference resistors 100, 102 and the remainder of the detector block so that such thermal impedances are each several times greater than, or an order of magnitude greater than, the thermal impedances that exist between the first and second reference resistors 100, 102 and the respectively nearest portions of the sensor resistor cavity 234. For example, the thermal impedances between the first and second reference resistors 100, 102 and the remainder of the detector block may be considered a thermal break, whereas the thermal impedances provided between the first and second reference resistors 100, 102 and the sensor resistor cavity 234 may be so low as to allow the temperatures of the first and second reference resistors 100, 102 to "track" (follow), without any significant delay, the temperatures of the respectively nearest portions of the cavity wall.

The reference resistors 100, 102 are selected to have particular temperature coefficients such that a change in the temperature of either of the two reference resistors 100, 102 causes a proportionate change in the resistance of the respective resistor. A spatial temperature gradient causes differing resistances that are exhibited by each of the first and second reference resistors 100, 102. The spatial temperature gradient in the portion of the detector block between the positions of the first and second reference resistors 100, 102 is thereby represented by a voltage derived from the operation of the reference signal means 108. The voltage represents an average of the differing resistances; a resulting temperature compensation signal from the first signal providing means 111 that represents an averaged value of the detector block temperature.

In the illustrated embodiment, either one of the first and second reference resistors 100, 102 is believed to be adequate to effect a compensation signal that is suitable for compensating for the effects of temporal temperature variation in the cavity wall. The combination of the first reference resistor 100 and the second reference resistor 102 is believed to be adequate to derive a compensation signal that is also suitable for compensating for the effects of a spatial temperature variation. Accordingly, one of the features of the present invention is the provision of a temperature compensation signal that is derived from operation of one or both of the first and second reference resistors 100, 102 in the reference signal means 108. Therefore, the illustrated embodiment employs compensation for the temporal and/or spatial temperature variations that would otherwise degrade the sensitivity and accuracy of the detector 200. Further, it should be recognized that the teachings of the present invention contemplate the use of third, fourth, etc. reference resistors (not shown), as may be located in certain embodiments at other positions relative to the sensor resistor 201 within the detector block.

Accordingly, FIG. 2 illustrates a variable voltage signal $V_T$ that represents the average temperature of the cavity wall in the immediate vicinity of the sensor resistor cavity 234. The voltage $V_T$ is provided on a signal line 116 for conditioning, when necessary, by a voltage gain circuit 120 and a voltage offset circuit 122. The output of the voltage offset circuit 122 then constitutes a temperature compensation signal $V_C$ that represents the average temperature of the wall of the sensor cavity 234.

In a particularly preferred embodiment, the sensor resistor 201 and the first and second reference resistor 100, 102 are located in spaced, co-planar arrangement within the detector block.

In still another embodiment, the temperature coefficients of the sensor resistor 201 and the reference resistors 100, 102 are matched.

A preferred embodiment of the second signal providing means 112 includes resistors 202, 203, and 204 connected to the sensor resistor 201 in a bridge circuit 208. The resistors 202–204 can be located remote from the sensor resistor 201 on (for example) a circuit board assembly; none of the resistors 202–204 need to be embedded or otherwise integrated with the detector block. In the embodiment shown in FIG. 2, the resistances $R_2$, $R_3$, and $R_4$ of the resistors 202, 203, and 204, respectively, determine the resistance $R_S$ of the sensor resistor 201 necessary to balance the bridge circuit 208. For example, if $R_3$ and $R_4$ are equal then $R_S$ must equal $R_2$ to balance the bridge. The second signal providing means 112 includes a first differential amplifier 205 having input terminals that are connected to balance nodes 206 and 207 of the bridge circuit 208. The output of the first differential amplifier 205 is connected to the common node of resistors 203 and 204 such that the amplifier 205 acts as a variable power supply for dynamically balancing the bridge 208.

The output of the first differential amplifier 205, representing the bridge voltage $V_A$ of the bridge circuit 208, is also connected to a a third signal providing means 113 that includes a non-inverting input in a second differential amplifier 210. The inverting input of the second differential amplifier 210 also receives the temperature compensation signal $V_C$ from the voltage offset circuit 122. The second differential amplifier 210 measures the amount of power dissipation in the bridge 208 based upon the value of the bridge voltage $V_A$ at various times. The measured change in power dissipation is then compensated according to the value of the temperature compensation signal $V_C$ so as to provide a detector output signal $V_O$ that is representative of the thermal conductivity of a detected sample constituent. The presence or concentration of one or more analytes in the sample fluid may then be indicated by providing the detector output signal $V_O$ to an information output device (not shown); of course, the detector output signal $V_O$ is also useful for other applications as known in the art. Suitable information output devices are known in the art and may include a strip chart recorder, a segmented or alphanumeric character display, a video display, or audio frequency transducer.

It will be recognized that although the functions provided by the first and second differential amplifiers 205, 210, the gain circuit 120, and the offset circuit 122 are each illustrated as a respective circuit element functional block, these functions may in alternative embodiments be subsumed into a single circuit element, or into other circuit elements that provide additional functions. Such circuit elements may be integrated within a data processor or other electronic systems for performing control, processing, and communication functions in addition to those described herein. Such circuit elements may be constructed from discrete and/or integrated circuit devices amenable to the practice of this invention and may include, e.g., one or more active devices such as microprocessors, microcontrollers, interface circuits, switches, logic gates, or equivalent logic devices capable of performing the functions described herein. The relevant processors may include random access memories and read-only memories in which information and programming can be stored and retrieved by known methods. Such memory may be used for storage and retrieval of operating condition parameters (such as voltage gain and voltage offset values, spatial temperature gradient thresholds, and so on).

Figure 3A:
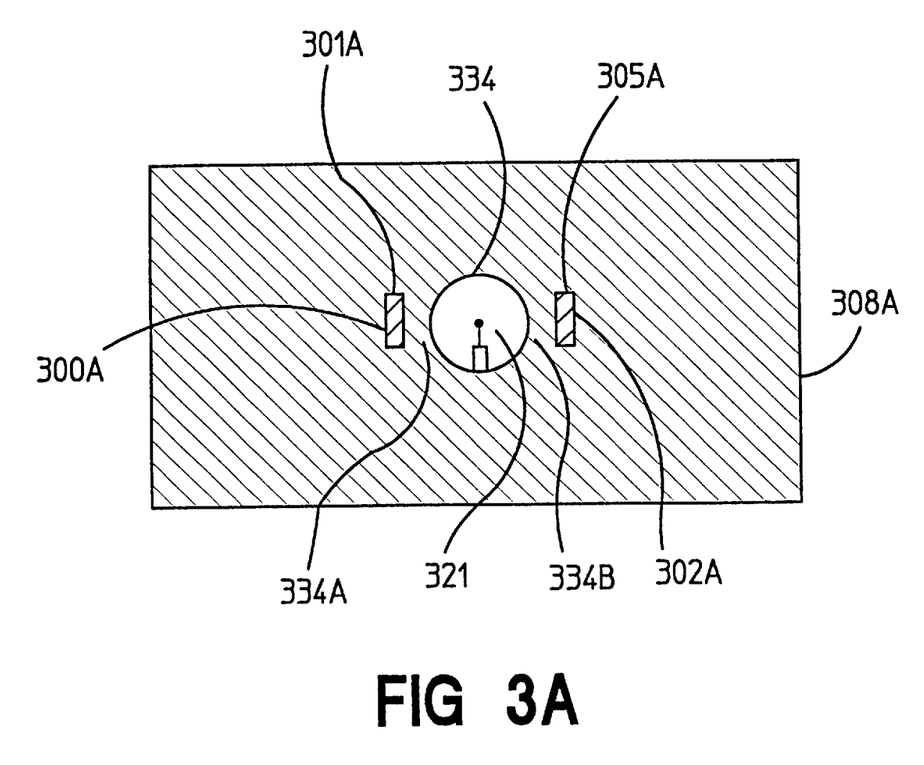
FIGS. 3A–3C and 4 are side sectional views of respective embodiments of a heated detector block that incorporates certain elements of the thermal conductivity detector of FIG. 2.
Figure 3B:
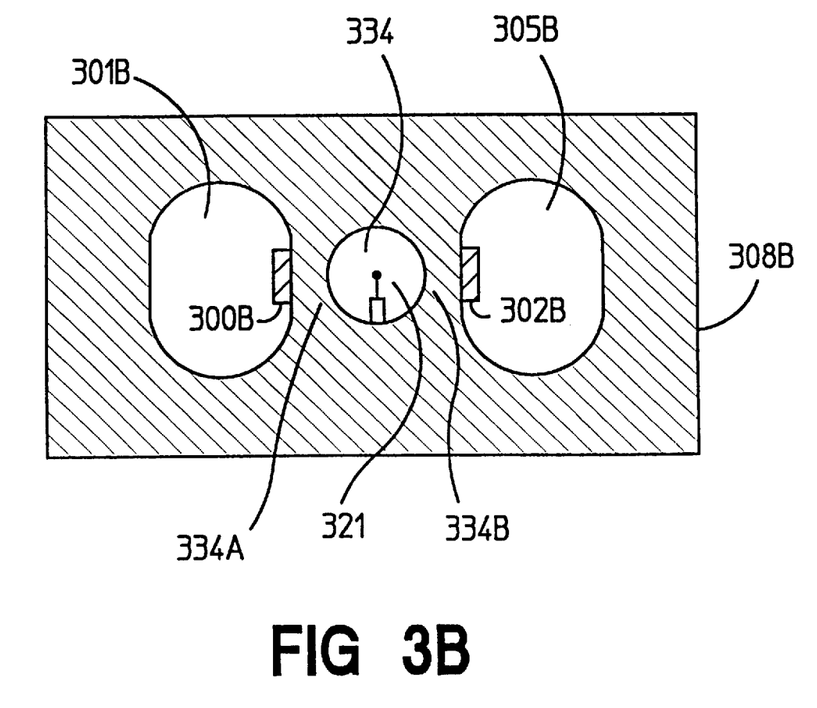
Figure 3C:
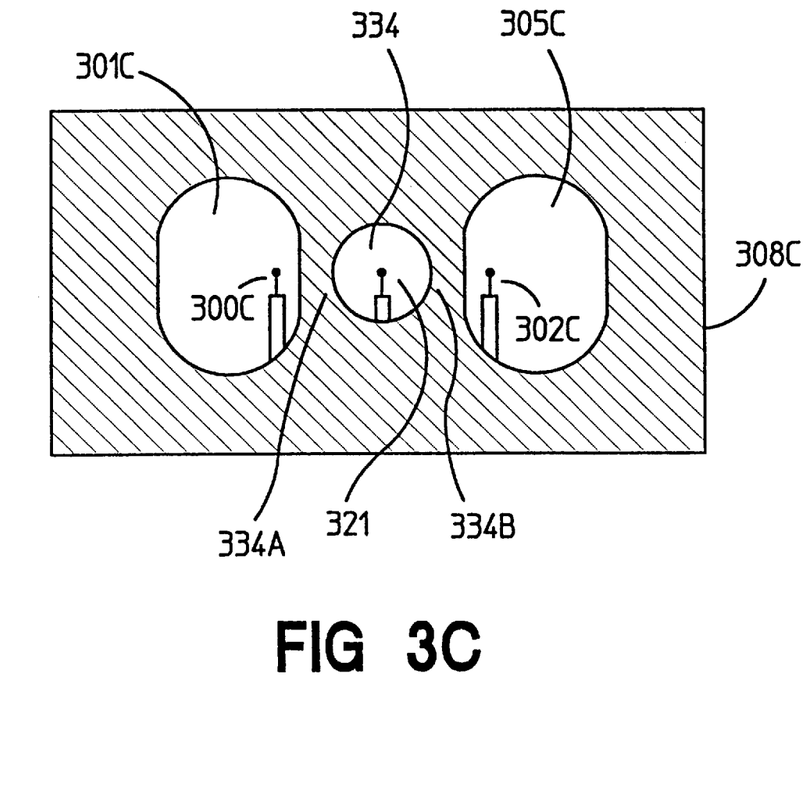

FIGS. 3A–3C respectively illustrate three alternative embodiments 308A, 308B, 308C of a preferred detector block. Each of the detector blocks 308B, 308C includes a sensor resistor cavity 334, a first reference resistor cavity 301A–C, and a second reference resistor cavity 305A–C. An embodiment of the sensor resistor 201 (FIG. 2) may be provided in the form of a resistive filament 321 that is centrally supported within the sensor resistor cavity 324. The resistive filament may be fabricated to include a filament of material such as tungsten or platinum having a resistance that is proportional to its temperature. Embodiments of the first reference resistor 100 may be provided in the form of electrically-insulated, resistive strip elements 300A, 300B, or resistive filament 300C; embodiments of the second reference resistor 102 may be provided in the form of electrically-insulated, resistive strip elements 302A, 302B, or resistive filament 302C. The embodiment illustrated in FIG. 3C (which employs resistive filaments 321, 300C, 302C) offers a manufacturing advantage in that each of such filaments may be similar or identical in construction, and the electronic circuitry required to monitor the signals provided by each filament is simplified.

The sensor resistor cavity 334 is preferably designed as a conduit for a controlled flow of a sample fluid containing one or more analytes to be detected, as described above. In contrast, the first reference resistor cavity 301A–301C and second reference resistor cavity 305A–305C are preferably sealed (self-contained). The first reference resistor cavity 301A–301C and second reference resistor cavity 305A–305C are respectively separated from the sensor resistor cavity 334 by cavity walls 334A, 334B. The first and second reference resistors 300A, 302A are embedded within the detector block 308A at respective locations proximate to the cavity walls 334A, 334B. Thus, the first and second reference resistors 300A, 302A fill respective first and second reference resistor cavities 301A, 305A such that each reference resistor and its cavity are one in the same. The first reference resistor cavities 301B, 301C and second reference resistor cavities 305B, 305C are larger in volume than the respective first and second reference resistors 300B, 300C, 302B, 302C. The first reference resistor cavities 301B, 301C and second reference resistor cavities 305B, 305C are preferably gas-filled. Alternatively, the first reference resistor cavity 301B and second reference resistor cavity 305B in FIG. 3B may be evacuated and sealed. Suitable techniques for construction of filaments and cavities in a detector block may be found in U.S. Pat. No. 4,170,126, the disclosure of which is incorporated herein by reference.

The resistive strip elements 300A, 302A are preferably embedded so as to be aligned with, and proximate to, the sensor resistor 321. The resistive strip elements 300B, 302B are similarly positioned but attached or embedded onto the surface of the first and second reference resistor cavities 301B, 305B so as to be aligned with, and positioned proximate to the sensor resistor 321. The filaments 300C, 302C are preferably supported on posts so as to be aligned with, and proximate to, the sensor resistor 321; filaments 300C, 302C are also electrically insulated with respect to the interior surfaces of the first and second reference resistor cavities 301C, 305C.

The present invention contemplates the use of a minimal cavity wall thickness in the cavity walls 334A, 334B in the vicinity of the resistive strip elements 300A, 300B, 302A, 302B and filaments 321, 300C, 302C so as to facilitate heat transfer for effecting the above-described compensation for temperature variations. Suitable electrical connections (not shown) to the resistive strip elements 300A, 300B, 302A, 302B or filaments 321, 300C, 302C may be provided through the body of detector blocks 308A, 308B, 308C in accordance with the circuit schematic presented in FIG. 2 using electrically-insulated, high-temperature connectors as known in the art.

Figure 4:
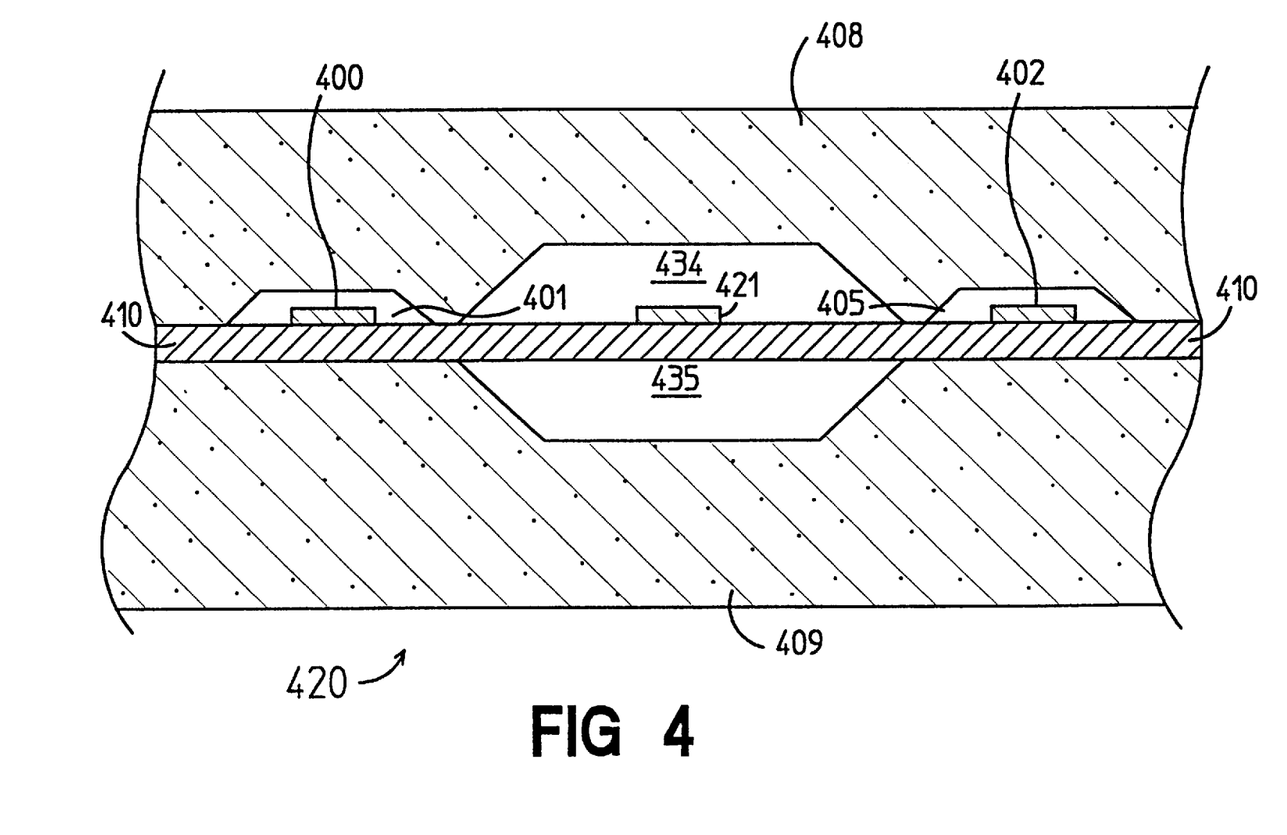

FIG. 4 illustrates a fourth alternative embodiment of a preferred thermal conductivity detector block fabricated as a microminiature planar thermal conductivity detector by use of techniques known in the arts of integrated circuit fabrication, micromachining, and microfabrication.

With reference to FIG. 4, a microminiature detector block 420 may include upper and lower substrates 408, 409 each constructed in the form of silicon chips which have been fabricated from one or more silicon wafers using batch processing steps. After fabrication, the upper and lower substrates 408, 409 may be superimposed, bonded together, and packaged by known techniques to form the microminiature detector block 420.

The construction of the detector block 420 may be generally understood as follows. An insulating layer 410 of electrical insulation, such as silicon dioxide, may be provided on the lower substrate 409. A flow channel in the form of a flow channel upper portion 434 (formed on the underside of the upper substrate 408) and a flow channel lower portion 435 (formed atop the lower substrate 409) may be provided by known etching techniques in the respective substrates. Individual resistive traces 400, 402, 421 of resistive material may be provided atop the insulating layer 410. The upper substrate 408 may be etched in certain areas such that resistive trace cavities 401, 405 are provided. The insulating layer 410 may be fully under etched in certain areas such that the portion of the insulating layer 410 that supports the resistive trace 421 is suspended within the flow channel. The insulating layer 410 may also be fully under etched in certain areas such that the the flow channel upper portion 434 and the flow channel lower portion 435 experience substantial fluid communication therebetween. Preferably, the resistive traces 400, 402, 421 and the upper and lower portions of the flow channel 434, 435 have similar lengths and are formed in parallel to the direction of the flow of the sample fluid in the flow channel.

The upper substrate 408 may be superimposed upon the lower substrate 409 such that the perimeters of the resistive trace cavities 401, 405 are aligned over the resistive traces 400, 402 and sealed on the insulating layer 410, and the perimeters of the flow channel upper portion 434 and flow channel lower portion 435 are sealed onto the insulating layer 410 to form the fluid-tight conduit necessary for the flow channel. (Ports (not shown) for directing a sample fluid into and through the flow channel may be formed in one or both of the upper and lower substrates 408, 409. For example, a sample fluid may be introduced through a port that communicates with one end of the combined upper and lower flow channel portions 434, 435 and allowed to exit the flow channel at a port that communicates with the opposing end of the flow channel.) The resistive trace 421 then may be employed as an embodiment of the sensor resistor 201 of FIG. 2, and the resistive traces 400, 402 may be employed as respective embodiments of the first and second reference resistors 100, 102 of FIG. 2.

While the embodiment illustrated in FIG. 4 has been described as being fabricated from silicon, other materials may be used. For example, other crystalline substrates such as gallium arsenide may be used, and modifications in the structure of the disclosed embodiments may be effected by use of differing patterns of etch-resistant coatings. In addition, specialized coatings such as silicon dioxide may be deposited or grown on one or more surfaces of the completed structure.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A thermal conductivity detector for detecting the thermal conductivity of a sample fluid, comprising:

a detector block having a cavity wall that defines a sensor resistor cavity for receiving a quantity of the sample fluid, said cavity wall being subject to a cavity wall temperature, and said cavity wall temperature being subject to spatial and temporal variations;

a sensor resistor located in the sensor resistor cavity and away from the cavity wall, said sensor resistor exhibiting a sensor resistance that is dependent on the temperature of said sensor resistor;

first signal providing means including reference signal means responsive to at least one of said temporal and spatial variations for providing a temperature compensation signal representative of said one of the spatial and temporal temperature variations wherein the reference signal means is located proximate to said cavity wall so as to be responsive to at least one of said temporal and spatial variations in the cavity wall temperature and wherein the reference signal means further comprises first and second reference resistors located in respective first and second reference resistor cavities separated from the sensor resistor cavity by the cavity wall, said first and second reference resistors being located proximate to said cavity wall, and said first and second reference resistors exhibiting respective first and second reference resistances the amounts of which are dependent on said cavity wall temperature, wherein said temperature compensation signal is provided in accordance with the amounts of said first and second reference resistances;

second signal providing means, connected to the sensor resistor, for providing a temperature sense signal that is related to the sensor resistance; and third signal providing means for receiving the temperature sense signal and the temperature compensation signal, and, in accordance with the temperature compensation signal, providing a detector output signal that is representative of the thermal conductivity of the sample fluid, said detector output signal being compensated for the effect of at least one of said spatial and temporal temperature variations.

2. The thermal conductivity detector of claim 1, wherein at least one of said first and second reference resistors further comprises a resistive strip element having a resistance that changes in proportion to changes in a temperature therein.

3. The thermal conductivity detector of claim 1, wherein at least one of said first and second reference resistors further comprises a resistive filament having a resistance that changes in proportion to changes in a temperature therein.

4. The thermal conductivity detector of claim 1, wherein the first signal providing means further comprises a means for determining an average value of said first and second reference resistances, and wherein the temperature compensation signal is provided in accordance with said average value.

5. The thermal conductivity detector of claim 4, wherein the first signal providing means further comprises a reference voltage source connected to the first and second reference resistors in a voltage divider network, wherein a node of the voltage divider network provides a variable voltage that is representative of an average temperature of the cavity wall.

6. The thermal conductivity detector of claim 1, wherein the second signal providing means includes a bridge circuit connected to said sensor resistor for providing a temperature sense signal that is related to a change in an amount of power delivered to said sensor and thereby representative of the thermal conductivity of the sample fluid.

7. The thermal conductivity detector of claim 6, wherein said second signal providing means further comprises a differential amplifier connected to the balance nodes of said bridge circuit configuration for outputting an output signal based upon a voltage difference between said balance nodes.

8. The thermal conductivity detector of claim 1, wherein the first signal providing means further comprises a voltage gain circuit and a voltage offset circuit for conditioning the temperature compensation signal.

9. A method for detecting an analyte in a sample fluid comprising the steps of:

providing a detector block having a cavity wall that defines a sensor resistor cavity for receiving a quantity of the sample fluid, said cavity wall being subject to a cavity wall temperature, and said cavity wall temperature being subject to spatial and temporal variations;

providing a heated sensor resistor in the sensor resistor cavity and away from the cavity wall, said sensor resistor exhibiting a sensor resistance that is dependent on the temperature of said sensor resistor;

providing a temperature sense signal that is related to the sensor resistance;

providing a temperature compensation signal means for generating a temperature compensation signal representative of at least one of said spatial and temporal temperature variations wherein the compensation signal means is located proximate to said cavity wall so as to be responsive to at least one of said temporal and spatial variations in the cavity wall temperature and wherein the compensation signal means further comprises first and second reference resistors located in respective first and second reference resistor cavities separated from the sensor resistor cavity by the cavity wall, said first and second reference resistors being located proximate to said cavity wall, and said first and second reference resistors exhibiting respective first and second reference resistances the amounts of which are dependent on said cavity wall temperature, and wherein said temperature compensation signal is provided in accordance with the amounts of said first and second reference resistances; and determining, in response to said temperature sense signal, a detector output signal that is representative of the thermal conductivity of the sample fluid, wherein said determination is compensated for the effect of said one of the spatial and temporal temperature variations according to said temperature compensation signal.

10. A method for detecting an analyte in a sample fluid comprising the steps of:

providing a cavity wall for defining a sensor cavity, the sensor cavity being suited for receiving the sample fluid;

providing, in the sensor cavity, a sensor resistive element having a resistance which is dependent on a temperature of said resistive element;

connecting said sensor resistive element in a bridge circuit configuration;

supplying a selectable amount of power to said bridge circuit configuration sufficient to maintain said sensor resistive element at a first predetermined temperature;

maintaining said cavity wall at a second predetermined temperature, so as to effect a temperature differential between said first and second predetermined temperatures;

measuring a quantity corresponding to said selectable amount of power;

providing first and second reference signal resistive elements in respective first and second reference signal cavities each separated from the sensor cavity by the cavity wall, each of said first and second reference signal resistive elements having a resistance dependent on a temperature of the respective reference signal resistive element;

providing a temperature compensation signal in response to the resistances of said first and second reference signal resistive elements; and determining, in response to said measured quantity and said temperature compensation signal, a detector output signal representative of the thermal conductivity of said analyte in the sample fluid.

* * * * *